United States Patent
Rasche

(10) Patent No.: US 7,845,851 B2
(45) Date of Patent: Dec. 7, 2010

(54) LOW-DOSE ISO-CENTERING

(75) Inventor: Volker Rasche, Erbach (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 88 days.

(21) Appl. No.: 12/065,616

(22) PCT Filed: Sep. 12, 2006

(86) PCT No.: PCT/IB2006/053242
§ 371 (c)(1), (2), (4) Date: Mar. 4, 2008

(87) PCT Pub. No.: WO2007/031945
PCT Pub. Date: Mar. 22, 2007

(65) Prior Publication Data
US 2008/0198972 A1  Aug. 21, 2008

Related U.S. Application Data

(60) Provisional application No. 60/717,089, filed on Sep. 14, 2005.

(51) Int. Cl.
*H05G 1/02* (2006.01)

(52) U.S. Cl. .......................... 378/195; 378/68; 378/69; 378/177; 378/196; 378/205; 378/208

(58) Field of Classification Search .................. 378/68, 378/69, 177, 195, 196, 205, 208
See application file for complete search history.

(56) References Cited

U.S. PATENT DOCUMENTS

| | | | |
|---|---|---|---|
| 5,457,724 A | 10/1995 | Toth | |
| 6,222,906 B1 | 4/2001 | Sakaguchi et al. | |
| 6,501,828 B1 * | 12/2002 | Popescu | 378/150 |
| 2002/0118280 A1 | 8/2002 | Medlar et al. | |
| 2003/0052879 A1 | 3/2003 | Barth | |
| 2004/0247069 A1 * | 12/2004 | Arai et al. | 378/4 |

FOREIGN PATENT DOCUMENTS

| | | |
|---|---|---|
| EP | 1092391 A1 | 4/2001 |
| WO | 03101300 A2 | 12/2003 |
| WO | 2005034757 A1 | 4/2005 |

* cited by examiner

*Primary Examiner*—Hoon Song
*Assistant Examiner*—Mona M Sanei

(57) ABSTRACT

Iso-centering a volume of interest (VOI) (170) within a patient (168) to undergo examination on a rotational X-ray apparatus (100) is achieved by taking two differently-angled pictures (S210) and updating positional settings (172) for the patient's table (112) responsive to respectively displayed centering of the VOI (152). Alternatively, the operator identifies respective VOI centers (S410, S450) for each of the two displayed pictures, and corresponding table movement is automatically calculated (S420).

17 Claims, 4 Drawing Sheets

LOW-DOSE ISO-CENTERING

CROSS REFERENCE TO RELATED APPLICATIONS

This application claims the benefit of U.S. provisional application Ser. No. 60/717,089 filed Sep. 14, 2005, which is incorporated herein by reference.

The present invention relates to iso-centering, on a rotational X-ray apparatus, a volume of interest within a patient and, more particularly to iso-centering in a manner that minimizes X-ray dosage to the patient.

Rotational X-ray imaging, which rotates the beam while acquiring X-ray data at angular intervals, affords accurate diagnosis and standardization in angiographic applications. A preliminary step is iso-centering the anatomy of interest or "volume of interest" (VOI), such as a structure in the heart. The iso-centering moves the patient's underlying table to center the VOI on an iso-center of a C-shaped or O-shaped frame. During the subsequent acquisition of diagnostic images, the frame assumes a particular position stationary except for circumferential rotation. That position is generally upright, although the frame may tip to slant either forwardly or backwardly to assume the stationary position. Some diagnostic pictures may be taken with one tilt of the frame, and later pictures may be taken with another tilt setting. Cranial and caudal tilt settings, for example, slant the beam with respect to the length of the patient's body. In one embodiment, an X-ray source attached to the frame faces within the frame toward a pickup device at the opposite side. In operation, as the X-ray beam traverses the inside of the frame, the beam passes through the iso-center, and, as the frame rotates circumferentially around its iso-center, so does the beam. The isocenter accordingly corresponds to an intersection of the centers of the angular instances of the beam as it rotates. In one embodiment, the C-frame is journaled into, and circumferentially slidable within, a supporting stand. Rotation of the frame correspondingly rotates the attached X-ray source. This rotation, in turn, rotates the beam to provide a number of X-ray acquisition images of the VOI from periodically-spaced angular views while the stand remains stationary. The frame is rotated over a predetermined angular range. For example, over the span of four seconds, 120 images may be taken at 1 degree intervals within a range of 120 degrees. Rotation over this span constitutes a single rotational run. The run may be repeated, with the frame remaining stationary at a given tilt or upright orientation, so that, for example, each view includes multiple images at different phases of the heart beat. Images of individual views may then be selected for analysis, since different views provide different information due, for example, to vessel overlap and foreshortening.

Accurate iso-centering minimizes the field of view (FOV) needed for a full coverage of the VOI over the entire rotation. Iso-centering typically involves panning the table at orthogonal horizontal directions, and varying the table height, while continuously taking X-ray pictures. The pictures are typically taken from two orthogonal views. The best centering of the VOI, based on the images, determines the corresponding optimal position of the table for subsequent rotational diagnostic X-ray imaging over the angular range.

However, during the positional adjustment of the table, the patient and the operator are unnecessarily exposed to X-rays.

Also, the two views for iso-centering are usually an AP (anterior-posterior) view, i.e., X-ray camera facing straight down at the patient's chest, and a lateral view. In finding, among the continuously taken pictures, the ones that best center the VOI, the operator normally navigates from picture pair to picture pair by estimating what table motion, in relation to the viewing angles, will bring the VOI into better view. The combination of AP and lateral views allows the operator or technician to more easily predict the impact table adjustment will have on the images to follow. This combination therefore facilitates navigation to the optimal picture pair corresponding to the iso-centering of the VOI.

Iso-centering is, as a result, practically constrained to the AP and lateral views.

To address the above-discussed shortcomings of the prior art, a centering device described hereinafter adjusts a support on which an object to be examined resides so as to center a volume of interest (VOI) the object contains. The device is configured for acquiring, from each radiation receiving site, an associated image carried on a respective incoming radiation beam. The acquired associated image includes a projection of the VOI. The device includes a centering controller for communicating an image acquired, and the included projection, for display on a screen. The device also specifies a new position for the support. Without need of further image acquisition, the device centers projection of the VOI with respect to a potential image. This is done by interactively updating display of the VOI on-screen in correspondence with the specified new position of the support.

In another aspect, a centering device determines how to adjust a support on which an object to be examined resides so as to center any arbitrary volume of interest (VOI) the object contains. The device acquires, from each radiation receiving site, an associated image carried on a respective incoming radiation beam. The acquired associated image includes a projection of the VOI. The device includes a centering controller for communicating an image acquired, and the included projection, for display on a screen. The device is operable to identify, from output of a user input device, a location on-screen of the center of the displayed projection and to calculate a movement of the support based on the identified location.

Details of the invention disclosed herein shall be described with the aid of the figures listed below, wherein.

Figure 1:
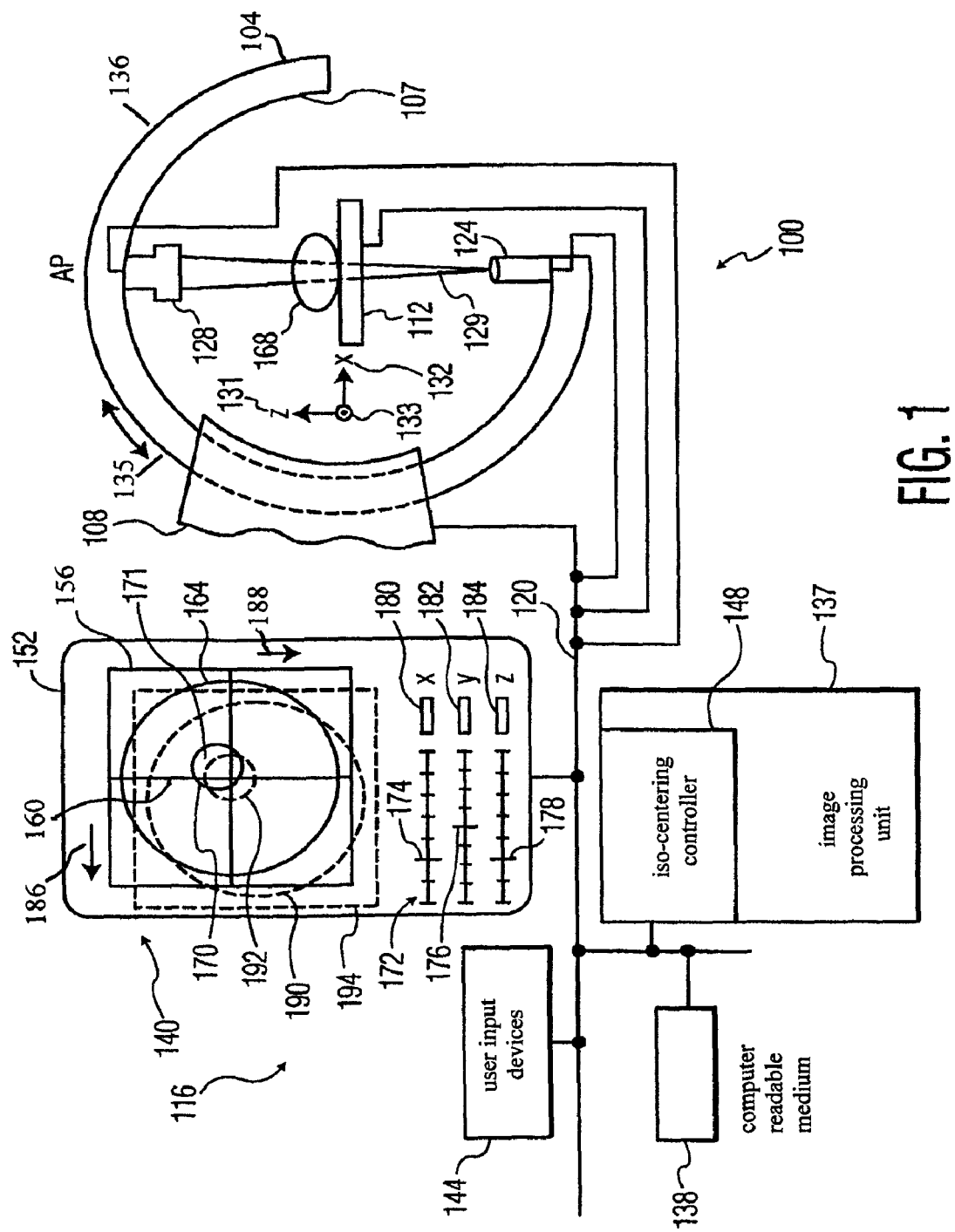
FIG. 1 is a schematic diagram of a rotational X-ray imaging apparatus according to the present invention.

FIG. 1 depicts, by way of illustrative and non-limitative example, a rotational X-ray imaging apparatus 100 according to the present invention. The apparatus 100 includes a C-arm 104 slidable within a stand 108, a patient-supporting table 112 and a centering device 116. The C-arm 104, stand 108 and table 112 have respective drives (not shown) and are connected to the centering device 116 on a power and data bus 120.

The C-arm 104 has, along its inner periphery, an X-ray source 124, and an X-ray pickup device 128 that functions as an X-ray receiving site. In the vertical orientation of the source 124 and device 128 shown in FIG. 1, the X-ray beam 129 acquires image data for an anterior-posterior (AP) view. The AP view is in the direction of the z-axis 131. The lateral view is orthogonal to the AP view and lies along the x-axis 132. The y-axis 133 is normal to FIG. 1. Angular range limits 135, 136 are shown in FIG. 1 to define, as one example, a 120 degree angular range over which the beam 129 is rotatable, by virtue of rotation of the C-arm 104. Alternatively, an O-shaped arm may be designed to remain stationary during operation while the source and pickup device move along the arm, or while multiple source/pickup device pairs at intervals along the arm are activated/deactivated.

The centering device 116 includes a control and image processing unit 137, a memory 138, a monitor 140, and user input devices 144. The control and image processing unit 137 incorporates an iso-centering controller 148 which may be implemented in software, hardware, firmware or any combination of software, hardware and firmware. The memory 138 would typically include, in addition to a non-volatile component, volatile working memory from which to calculate prospective X-ray views, and prospective table positions, in the course of iso-centering. Read-only-memory (ROM), random-access memory (RAM), flash and other types of memory may be used. The centering device 116 can include a separate processor (not shown) for diagnostic image acquisition after the iso-centering, or the functionality may be integrated with the iso-centering controller 148.

The monitor 140 features a screen 152 with an image acquisition area 156 that features a centering graticule 160. As an example, the outline of a human heart 164 is shown on-screen, corresponding to that of the patient 168 to be examined, who is lying on the table 112. A specific volume of interest (VOI) 170 within the heart 164 is projected off-center on-screen. In particular, an identifiable center 171 of the VOI 170 is generally, before iso-centering, offset from the center of the centering graticule 160. The bottom of the screen 152 provides table-movement-directional-component sliders 172, including an x-component slider 174, and y-component slider 176, and z-component slider 178. The sliders 172 are preferably shifted by means of a screen cursor (not shown) the operator can drag using a mouse or other of the input devices 144. Alternatively, the screen 152 may be implemented as a touch screen, allowing the operator to shift the sliders 172 by means of a finger tip. Specification of table movement in a component direction can instead be realized by other graphical user interface (GUI) means, or by manual actuation of controls. Preferably, the specifying, on-screen or otherwise, does not automatically move the table 112.

Next to each of the component sliders 174, 176, 178 is located the respective positional-reading window 180, 182, 184. Respectively offset in the directions of the illustrative arrows 186, 188 and indicated by dotted line, FIG. 1 shows, by way of further example, an updated outline 190 of the heart 164, an updated projection 192 of the VOI 170, and an updated image-acquisition-area 194. Although FIG. 1 shows, for simplicity of demonstration, merely a single image acquisition area 156, the screen 152 is preferably operable to simultaneously display two image acquisition areas for two respective views of the VOI 170 at respectively different angles. Alternatively, the two views may be selectively swapped, one at a time, into the single image acquisition area 156.

Figure 2:
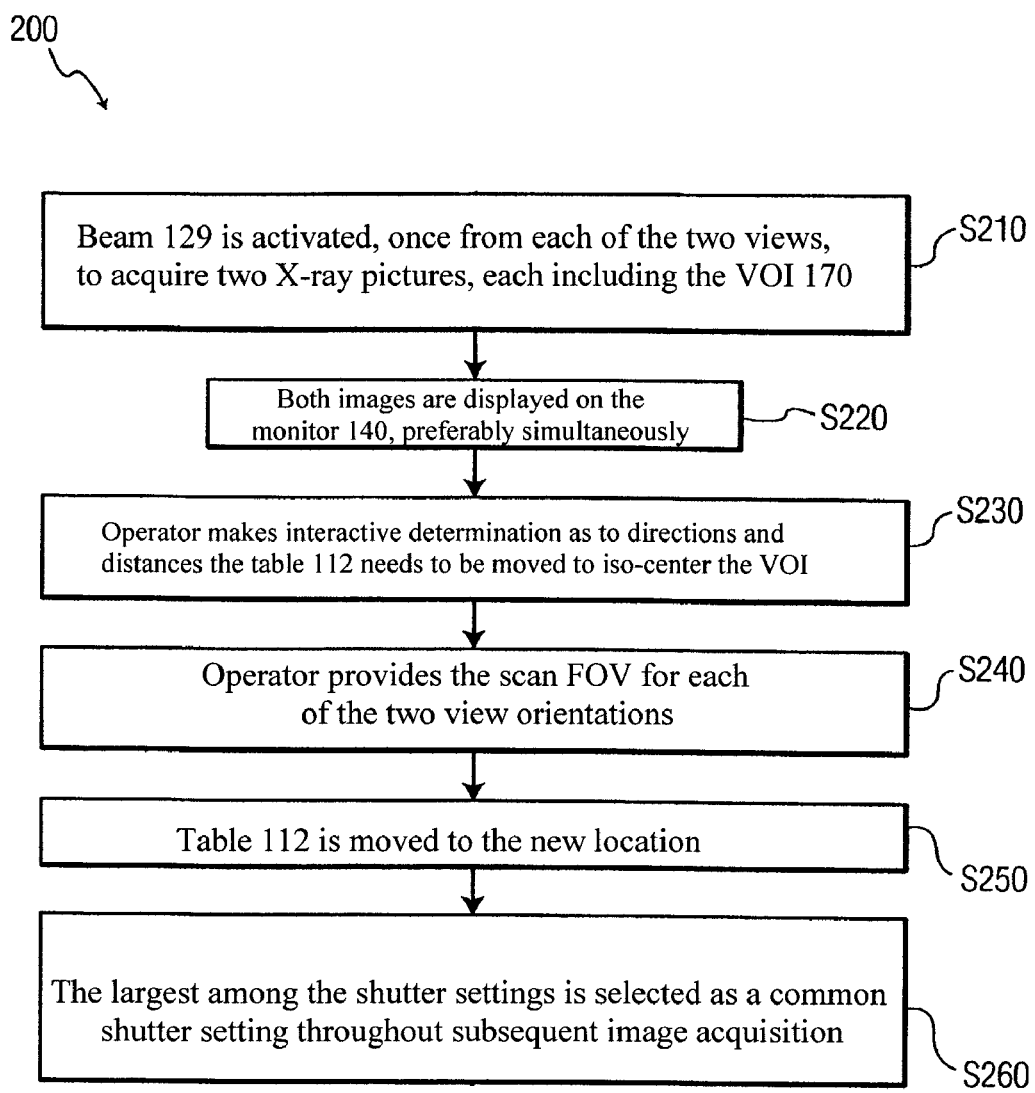
FIG. 2 is a flow chart of an imaging initialization process according to the present invention.

FIG. 2 shows an exemplary imaging initialization process 200 for the rotational X-ray imaging apparatus 100. To iso-center the VOI 170 on the C-arm 104, only two images are required. Thus, in the course of iso-centering, the consequent X-ray dosage to the patient 168 is far less than that of the prior art continuous-exposure technique. Preferably, the two views chosen are the AP view and the lateral view, although, as an alternative according to an embodiment of the present invention, other viewing angles may be used.

The patient 168 lies down on the table 112 and is guided to assume a position at which the beam 129 would at least partially cover, and preferably encompass fully, the VOI 170. To achieve coverage, drives for the C-arm 104 and/or the table may be actuated, by manual controls and/or by means of the user input devices 144. The VOI 170 has been arbitrarily selected by the clinician, as by guiding the patient into a particular position on the table 112 and/or guiding the C-arm 104 into position.

The beam 129 is then activated, once from each of the two views, to acquire two X-ray pictures, each including the VOI 170 (step S210). The anatomy of interest may, for instance, consist of an occluder balloon and its surroundings, the balloon residing within a blood vessel of the heart for restricting flow of blood when inflated. Thus, it would be desirable to center, on the occluder balloon, the diagnostic X-ray scans to be performed. Each of the two views just taken would generally show the occluder balloon somewhat off-center. Thus, one objective of iso-centering is to maneuver the VOI 170 so that subsequent pictures at each of the two views would feature the VOI centered. Preferably, the two views are mutually orthogonal, or nearly so, to likewise center the VOI, on the C-arm iso-center, with respect to any of the other angles along the rotational run to be performed. Once centered, the field of view (FOV) of the X-ray scan is preferably fitted, e.g., by contraction or expansion, to the desired boundaries of the VOI.

As a preliminary step after acquisition of the two single X-ray views, both images are displayed on the monitor 140, preferably simultaneously (step S220). The operator makes an interactive determination as to in what directions, and by what corresponding distances, the patient-supporting table 112 needs to be moved to iso-center the VOI (step S230). Preferably, the interaction involves automatic update of the image acquisition areas 156 in correspondence with the display that would result from image acquisition from the patient 168 at the new location. Once the determination is made, the operator then provides the scan FOV for each of the two view orientations (step S240). This may be done by marking off points, on the updated image-acquisition-areas 194, to define the desired boundary of the VOI, and therefore shutter settings for the X-ray pickup device 128 for each of the two views. In preparation for diagnostic image acquisition, the table 112 is moved to the new location (step S250). The table 112 can move automatically to the new table location determined in step S230, or the operator can actuate manual controls based on the displayed new slider settings. Preferably, the largest among the shutter settings is selected as a common shutter setting throughout subsequent image acquisition (step S260). At some point in acquiring X-ray pictures, it might be desirable to tilt the C-arm 104, or change its tilt, before resuming acquisition. If a change in the VOI 170 is involved, or if the tilting changes the C-arm iso-center, the whole initialization process 200 is repeated.

Figure 3:
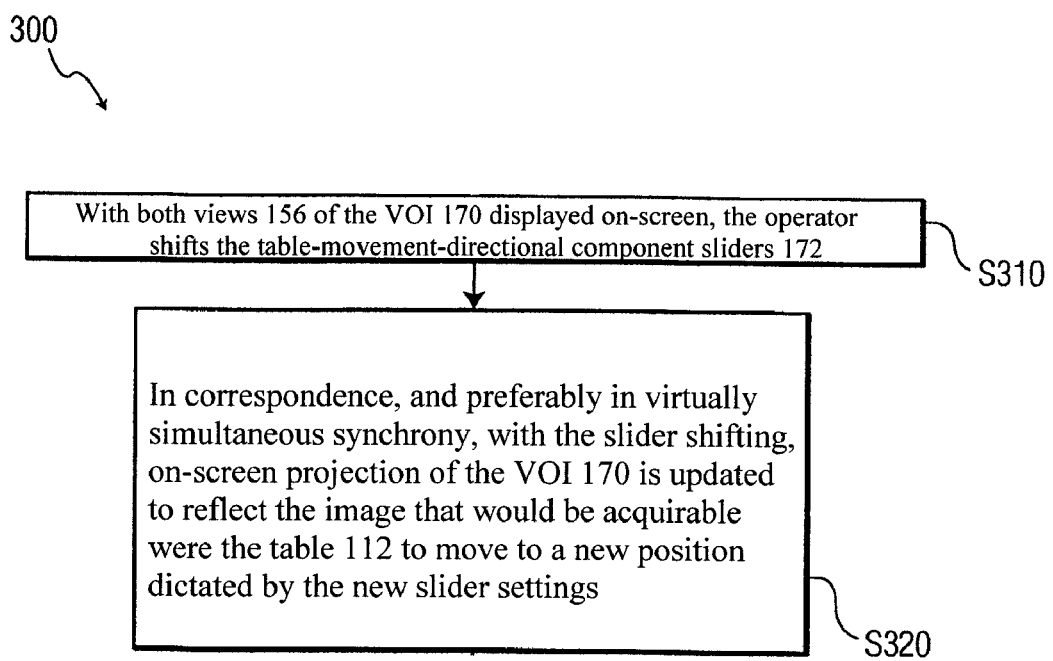
FIG. 3 is a flow chart of a first embodiment of a table-movement determining process according to the present invention.

FIG. 3 represents, in a first embodiment, a table-movement determination process 300 corresponding to step S230, in accordance with the present invention. With both views 156 of the VOI 170 displayed on-screen, the operator shifts the table-movement-directional component sliders 172 (step S310). It is also possible to shift the sliders 172 with a single view 156 on the on-screen. In correspondence, and preferably in virtually simultaneous synchrony, with the slider shifting, on-screen projection of the VOI 170 is updated to reflect the image that would be acquirable were the table 112 to move to a new position dictated by the new slider settings (step S320). Thus, in the case of an AP view, for example, vertical translation of the table 112 zooms the projection 192 in or out. Horizontal translation correspondingly translates the display which thereby appears as the offsetted projection 192. Analogously, for the lateral view, i.e., along the x-axis 132, horizontal translation along the x-axis zooms the projection 192 in or out, and translation in the y-axis 133 or z-axis 131 translates the projection. At an angular view exactly between the AP and lateral views, i.e., at 45 degrees, the AP and lateral reactions for movement in any given component direction are equally averaged for that component. Thus, for example, at such a viewpoint, vertical translation upward will zoom in the projection 192, and translates it sideways in the sideways direction shown in FIG. 1. At other angular views, the AP and lateral reactions can be correspondingly interpolated to update the projection 192. Alternatively, a view at the desired angle can be derived from a three-dimensional reconstruction performed based on the two or more acquisitions at respective angles.

By shifting the sliders 172 to center the updated projection 192 on the centering graticule 160, as described above, the operator is able to interactively derive the required component-direction settings for iso-centering. At any given moment, the updated projection 192, which affords interaction, approximates, and positionally corresponds to or matches, a projection of the VOI in a potential image that could be acquired if the table 112 were to be moved according to the current settings of the sliders 172.

Figure 4:
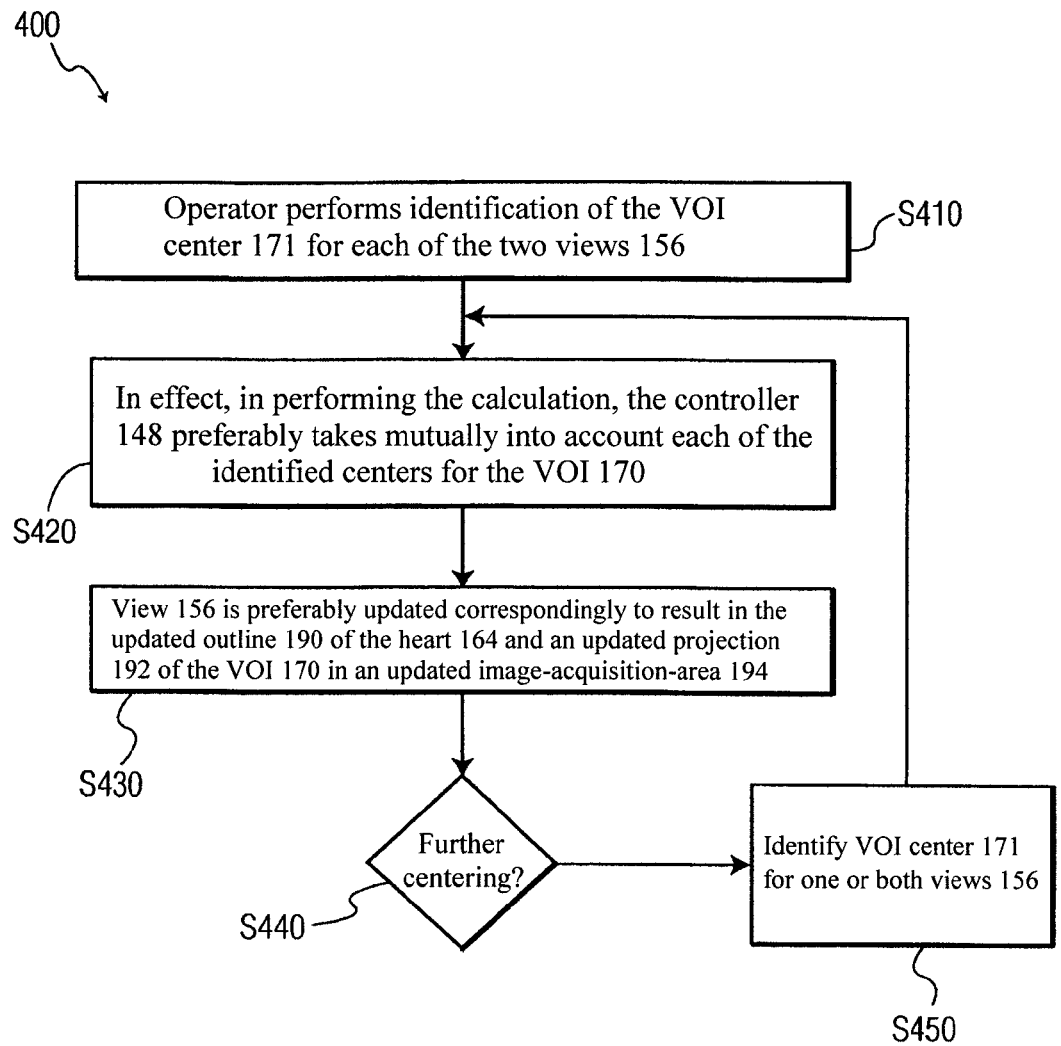
FIG. 4 is a flow chart of a second embodiment of a table-movement determining process according to the present invention.

FIG. 4 represents, in a second embodiment, a table-movement determination process 400 corresponding to step S230, in accordance with the present invention. The operator indicates on-screen a location on the screen 152 of the center 171 of the displayed VOI 170. The operator performs the identification of the VOI center 171 for each of the two views 156 (step S410). Preferably, the views 156 are simultaneously displayed. The identification may be made by means of a user input device 144, such as a mouse or light pen, or by means of the operator's fingertip on a touch screen 152. Alternatively, an on-screen cursor can be designed to move according to commands the operator delivers orally. The identified centers 171 of the respective views 156 preferably would, but in practice generally will not exactly, coincide at a single point of intersection within the VOI 170. As another alternative, the operator may, instead of indicating on-screen the center 171, trace on-screen to define what the operator thereby specifies to be the boundary of the VOI 170. Logic within the iso-centering controller 148 can then determine a center of the on-screen projection within the boundary according to any known and suitable method, such as by finding the smallest circle into which the boundary may be inscribed.

Next, the iso-centering controller 148 calculates movement of the table 112. The movement is that which would center the VOI center 171, identified directly or indirectly by the operator, within the X-ray beam 129 that has acquired the VOI image for which the operator has identified the center. The difference between the screen coordinates of the identified center 171 and those of the center of the centering graticule 160 imply corresponding movement of the table 112 to a new position that can reside anywhere along the centerline of the X-ray beam 129 that has acquired the image. Thus, for example, update to an AP view 156 would normally involve a mere translation in the x-y plane, but could, in addition, include translation along the z-axis 131. The same principle holds for any view 156. In the case of a single view 156, the new position may correspond to the point on the centerline that is closest to the present position.

However, taking into account the new table-position line for the other view 156 may dictate selection of a different point on the centerline of the first view.

This different point would ideally be decided as the point of intersection between the two centerlines, but, as mentioned above, the two lines generally will not intersect exactly. Therefore, the point on one line closest to the other line is preferably chosen. Accordingly, the new table location calculated for one view 156 differs slightly from that for the other view 156. These two new locations are averaged to yield the location to which the sliders 172 are updated on-screen.

In effect, in performing the calculation, the controller 148 preferably takes mutually into account each of the identified centers for the VOI 170 (step S420).

In addition to updating the displayed slider settings 172, the view 156 is preferably updated correspondingly to result in the updated outline 190 of the heart 164 and an updated projection 192 of the VOI 170 in an updated image-acquisition-area 194 (step S430). The outlines 190 and projections 192 for both views are preferably updated simultaneously on-screen.

Since, as discussed above, identification on-screen of the VOI center 171 merely approximates the center, leading to an averaging of separately calculated new table locations based on the respective views, the updated projections 192 may still appear slightly off-center on the screen 152. If further centering is therefore necessary (step S440), the operator may again identify the center 171 for one or both views 192 (step S450), to trigger recalculation at step S420.

Advantageously, since the operator merely points to the VOI center 171 interactively, and need not estimate the kinds of movement components that would iso-center the VOI, the two views are not restricted to the AP and lateral views.

In either of the two iso-centering embodiments set forth above, the dosage to the patient is limited to two X-ray pictures, thereby minimizing potentially harmful exposure of the patient to radiation. In addition, iso-centering is quick and accurate.

While there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it should be recognized that structures and/or elements and/or method steps shown and/or described in connection with any disclosed form or embodiment of the invention may be incorporated in any other disclosed or described or suggested form or embodiment as a general matter of design choice.

The invention claimed is:

1. A centering device for adjusting a support on which an object to be examined resides so as to center any arbitrary volume of interest said object contains, said device being configured for acquiring, from each of two views taken at different angles of rotation of an arm of an imaging apparatus, an associated image carried on a respective incoming radiation beam, each radiation beam having a centerline, wherein the centerlines of the radiation beams do not coincide at a single point of intersection within the volume of interest and each centerline has a point that is closest to the other centerline, the acquired associated image including a projection of said arbitrary volume, said device comprising:
   a display;
   a user input device; and
   a centering controller configured for:
      acquiring the two associated images;
      displaying the two associated images and the included projections of said arbitrary volume on the display;
      accepting from the user input device a location of a center or boundary of each of the displayed projections of said arbitrary volume; and calculating movement of said support based on an average location determined by the point on either centerline that is closest to the other centerline.

2. The centering device of claim 1, wherein the two centerlines are mutually orthogonal.

3. The device of claim 1, the calculating taking into account a plurality of locations.

4. The device of claim 1, wherein the displaying reflects an update to said movement.

5. The device of claim 1, wherein said controller is further configured for:
   determining, for each boundary of the displayed projections, a respective radiation shutter setting.

6. A rotational X-ray imaging apparatus comprising the centering device of claim 1.

7. A method for centering a support on which an object to be examined resides so as to center any arbitrary volume of interest said object contains, the method comprising:
   acquiring from each of two views taken at different angles of rotation of an arm of an imaging apparatus an associated image carried on a respective incoming radiation beam, each radiation beam having a centerline, wherein the centerlines of the radiation beams do not coincide at a single point of intersection within the volume of interest and each centerline has a point that is closest to the other centerline, the acquired associated image including a projection of the arbitrary volume;
   displaying the two associated images and the included projections of said arbitrary volume on a display;
   accepting from a user input device a location of a center or boundary of each of the displayed projections of said arbitrary volume; and
   calculating movement of the support based on an average location determined by the point on either centerline that is closest to the other centerline.

8. The method of claim 7, wherein the two centerlines are mutually orthogonal.

9. The method of claim 7, the calculating taking into account a plurality of locations.

10. The method of claim 7, wherein the displaying reflects an update to said movement.

11. The method of claim 7, wherein the controller is further configured for determining for each boundary of the displayed projections a respective radiation shutter setting.

12. A non-transitory computer readable storage medium comprising instructions for performing steps of a method for centering a support on which an object to be examined resides so as to center any arbitrary volume of interest said object contains, the method comprising:
   acquiring from each of two views taken at different angles of rotation of an arm of an imaging apparatus an associated image carried on a respective incoming radiation beam, each radiation beam having a centerline, wherein the centerlines of the radiation beams do not coincide at a single point of intersection within the volume of interest and each centerline has a point that is closest to the other centerline, the acquired associated image including a projection of the arbitrary volume;
   displaying the two associated images and the included projections of said arbitrary volume on a display;
   accepting from a user input device a location of a center or boundary of each of the displayed projections of said arbitrary volume; and
   calculating movement of the support based on an average location determined by the point on either centerline that is closest to the other centerline.

13. The computer readable storage medium of claim 12, wherein the two centerlines are mutually orthogonal.

14. The computer readable storage medium of claim 12, the calculating taking into account a plurality of locations.

15. The computer readable storage medium of claim 12, wherein the displaying reflects an update to said movement.

16. The computer readable storage medium of claim 12, wherein the controller is further configured for determining for each boundary of the displayed projections a respective radiation shutter setting.

17. A rotational X-ray imaging apparatus comprising the computer readable storage medium of claim 12.

* * * * *